United States Patent [19]

Linde

[11] Patent Number: 5,048,947
[45] Date of Patent: * Sep. 17, 1991

[54] PROCESS FOR MEASURING EYE MOVEMENT

[76] Inventor: Lucille M. J. Linde, 1954 18th Ave., Greeley, Colo. 80631

[*] Notice: The portion of the term of this patent subsequent to Apr. 4, 2006 has been disclaimed.

[21] Appl. No.: 502,450

[22] Filed: Mar. 30, 1990

[51] Int. Cl.$^5$ .............................................. A61B 3/02
[52] U.S. Cl. ...................................... 351/224; 351/226
[58] Field of Search ................ 351/209, 210, 224, 226

[56] References Cited

U.S. PATENT DOCUMENTS

| | | | |
|---|---|---|---|
| 2,221,936 | 11/1940 | Jobe | 351/224 |
| 2,451,932 | 10/1948 | Ellis | 351/224 |
| 4,818,097 | 4/1989 | Linde | 351/224 |

Primary Examiner—Paul M. Dzierzynski
Attorney, Agent, or Firm—Dean P. Edmundson

[57] ABSTRACT

An improvement is described in regard to a target which is useful in a process for measuring eye movement of a subject. The target includes a support member with a flat or planar bottom surface which can rest upon the top edge of the arcuate member which is used in measuring eye movement. The target can be easily moved along the arcuate member in a smooth and steady manner, with the support member resting on the arcuate member.

6 Claims, 1 Drawing Sheet

PROCESS FOR MEASURING EYE MOVEMENT

FIELD OF THE INVENTION

This invention relates to processes for measuring eye movement. More particularly, this invention relates to an improved visual target for use in a process for measuring eye movement. Even more particularly, this invention relates to use of a visual target in a technical process for measuring a person's ocular tracking ability.

BACKGROUND OF THE INVENTION

In my previously issued U.S. Pat. No. 4,818,097 (entitled Ocular-Pursuit Measuring), incorporated herein by reference, I described a technical process for a quick, simple, objective, and accurate measurement of an individual's ocular tracking ability. The process involves, in part, the use of an ocular-pursuit measuring instrument comprising an arcuate member pivotally mounted at its midpoint to the upper end of a stand or leg member in a manner such that the arcuate member can be pivoted about an axis passing through the midpoint perpendicular to the axis of the stand or leg supporting the arcuate member.

The arcuate member includes a graduated scale (e.g., in one-half inch increments) extending outward from the midpoint of the arcuate member in both directions.

A target is moved along the arcuate member from the midpoint as far as smooth eye movement by such person following the target is completed accurately. That is, when eye movement becomes irregular (e.g., jerky, unable to focus on the target) the testing starts over again (at a lower starting point) and the target is moved outwardly from the midpoint and then back again in successively increasing distances until the second point of nystagmus is observed. The number of units (e.g., to the nearest half inch) between the midpoint of the arcuate member and the last or maximum point where smooth eye movement was completed accurately are then recorded, i.e., the farthest point of smooth eye movement is then recorded. This technical unique process is used on each eye individually and on both eyes together to determine each subtest score. Subtest scores are then totalled for one score.

The technique of my prior patent provides a means of indicating the general neurological health as reflected in results from ocular pursuit ability and enables treatment of the individual with motor perceptual training to improve neurological development and performance. It has also been found that an individual's ocular tracking score correlates beyond the 0.01 level of significance with the individual's score on the CTBS academic achievement test (California Test of Basic Skills).

The procedures of my prior invention are useful and effective when used with individuals of all types, both for measuring and improving their ocular tracking ability and improving their neurological development. For example, individuals of the following types may be improved with the techniques of motor-perceptual training: (a) the learning disabled (e.g., those with hearing and visual impairment, mentally retarded, average, minority), (b) the motorially handicapped (e.g., those suffering from cerebral palsy, muscle spasms, epilepsy, scoliosis), and (c) those with special learning disabilities (e.g., aphasic, dyslexic) and gifted.

The ocular pursuit measuring instrument used in the techniques described in my prior patent is used for educational purposes in evaluating and diagnosing an individual's ocular tracking ability. The examiner observes the moving eye and records the ability of the eye to follow a target without irregularity or jerkiness in eye movement. Then both eyes are tested together following a moving target.

Thus, the technique described in my prior patent utilizes the ocular pursuit measuring instrument to obtain a neurologically oriented objective examination for educational diagnosis, evaluation, and prescribed motor-perceptual training. Because the examiner observes the moving eye(s), the examiner is able to determine accurately and quickly where smooth eye movement is interrupted by jerkiness or inability to focus on a target. Some perimeters require the use of many items of equipment such as the use of lights, photographs, mirrors, and light beams. This ocular pursuit measuring instrument does not require any special equipment such as this.

Other advantages of the process of my prior patent are also apparent. There is no need for the examiner to communicate with the subject being examined other than to request the subject to follow the target with his eyes. Even very young subjects may be easily tested. The subjects do not have to be able to read in order to be tested in the process of such invention. Also, the subject does not operate the instrument. Further, there is no need for specially equipped rooms for conducting the examination. Training of the examiner would not be time-consuming. The expertise develops through experience and sensitivity of the examiner in observing eye movement.

By using the process of my prior patent for measuring ocular tracking ability, motor-perceptual training has been demonstrated to improve oculomotor ability in as few as 5.5 to 7.5 hours of treatment with results at or beyond the 0.01 level of statistical significance.

In my prior patent I described moving a target along the arcuate member for the subject to follow with his or her eyes. The person conducting the test typically moves the target (e.g., a pencil, or colored tip on the end of a pointer) along the arcuate member by holding the target with one hand in a manner such that the target is in close proximity to the arcuate member. Although such procedure can be used effectively, it does require that the person holding and moving the target be quite steady so as to avoid jerky and uneven movement of the target. Since a purpose of the ocular-pursuit measuring is to determine the point along the arcuate member where smooth eye movement is interrupted, any jerky or unsteady movement of the target during the testing can interfere with the test results. In other words, jerky movement of the target itself can interrupt smooth movement of the subject's eyes if done by an inexperienced individual or one who does not have a steady hand. The end result is that it would be possible for a false test score to be recorded.

SUMMARY OF THE INVENTION

It is an object of the present invention to provide an improved target for use in a process for measuring eye movement.

It is another object of the present invention to provide an improved target for use in conjunction with an arcuate member in a process for measuring eye movement.

In accordance with the present invention there is provided an improved process for measuring eye movement of a subject by moving a target along an arcuate member positioned ahead of the subject. The improvement comprises use of a visual target which is supported at least in part on the arcuate member.

Because the target is supported at least in part on the arcuate member, the target can be moved along the arcuate member very smoothly and easily without jerky movements. This greatly facilitates proper testing of the subject. By resting the target on the arcuate member, the target cannot move up and down as it is moved along the arcuate member.

Other advantages of the present invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
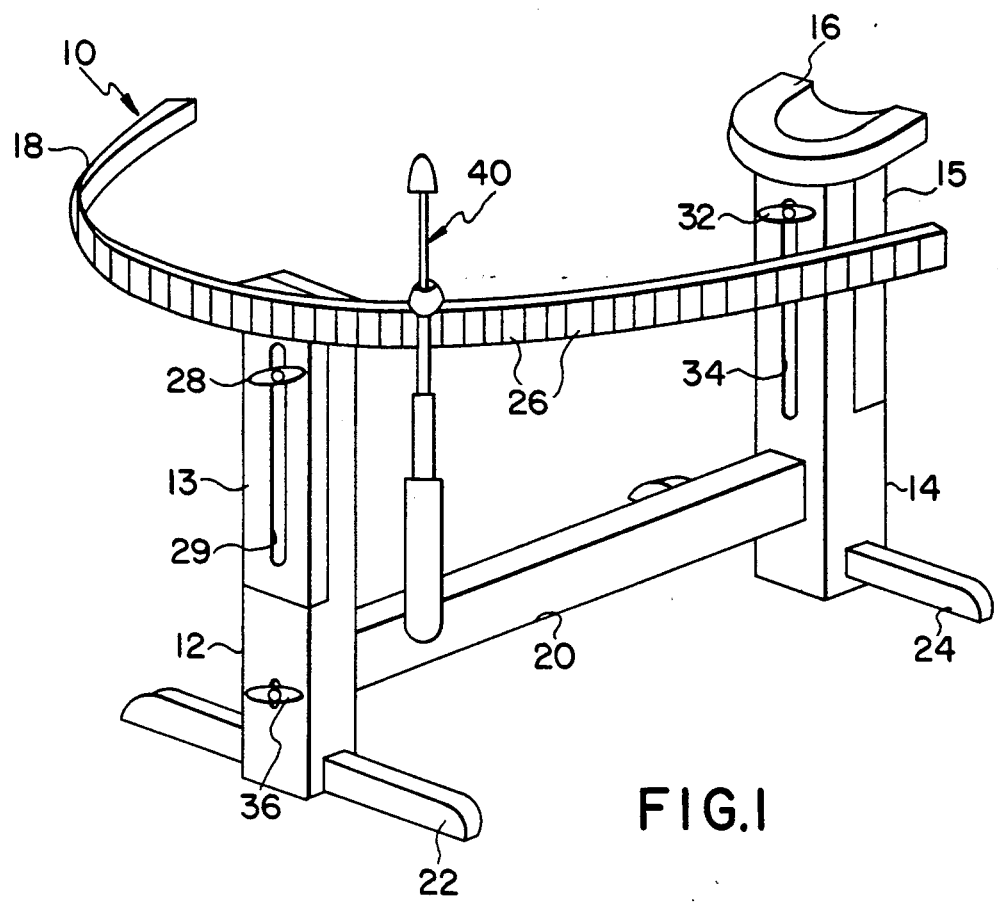
FIG. 1 is a perspective view of an arcuate member and an improved target of the present invention.

In FIG. 1 there is illustrated apparatus 10 which can be used in measurement of eye movement of a subject. The apparatus includes a first upstanding leg member 12 and a second upstanding leg member 14. The leg members are spaced apart from each other and are connected by means of bar 20 which holds the leg members securely in relative position. Leg member 12 includes foot member 22 and leg member 14 includes foot member 24 which are affixed to the lower ends of the leg members to stabilize them. Connecting bar 20 may be disconnected, if desired, by loosening nut 36 on a threaded bolt extending through leg member 12 and into bar 20. A similar nut and bolt assembly secures the opposite end of bar 20 to leg member 14.

Leg member 14 includes chin support means 16 at the upper end. The person being tested places his or her chin on the support so that the head is stabilized during testing. Arm 15 is vertically adjustable so that the apparatus may accommodate individuals of different height. One manner of providing vertical adjustment is to secure the chin support means 16 to the upper end of arm 15 which is secured to leg member 14 by means of bolt 32. Leg member 14 includes a vertical slot 34, as shown in FIG. 1. A wing nut on the inside end of bolt 32 may be loosened when it is desired to raise the arm 15.

Arcuate member 18 is pivotably attached at its midpoint to the upper end of leg member 12. A bolt (not shown) is secured at one end to member 18 and extends through leg member 12. The arcuate member 18 may be pivoted about its midpoint in one direction or the other for various testing procedures. The arcuate member may be mounted outside of leg member 12 (as shown in the drawings), or it may be mounted inside of leg member 12, if desired. Also, means may be included to permit vertical adjustment of the arcuate member.

Arcuate member 18 includes a graduated scale along its periphery which is readable by the person conducting the testing. The scale may include any desired graduations 26, although it has been found that a tape measure having one-half inch graduations is very useful for the techniques of the present. A flexible tape measure may be easily and readily secured to the front face of the arcuate member.

The size of the arcuate member may vary, although it has been found that a radius of curvature of the arcuate member is preferably in the range of about 20 inches. The arcuate member is preferably semi-circular.

Figure 2:
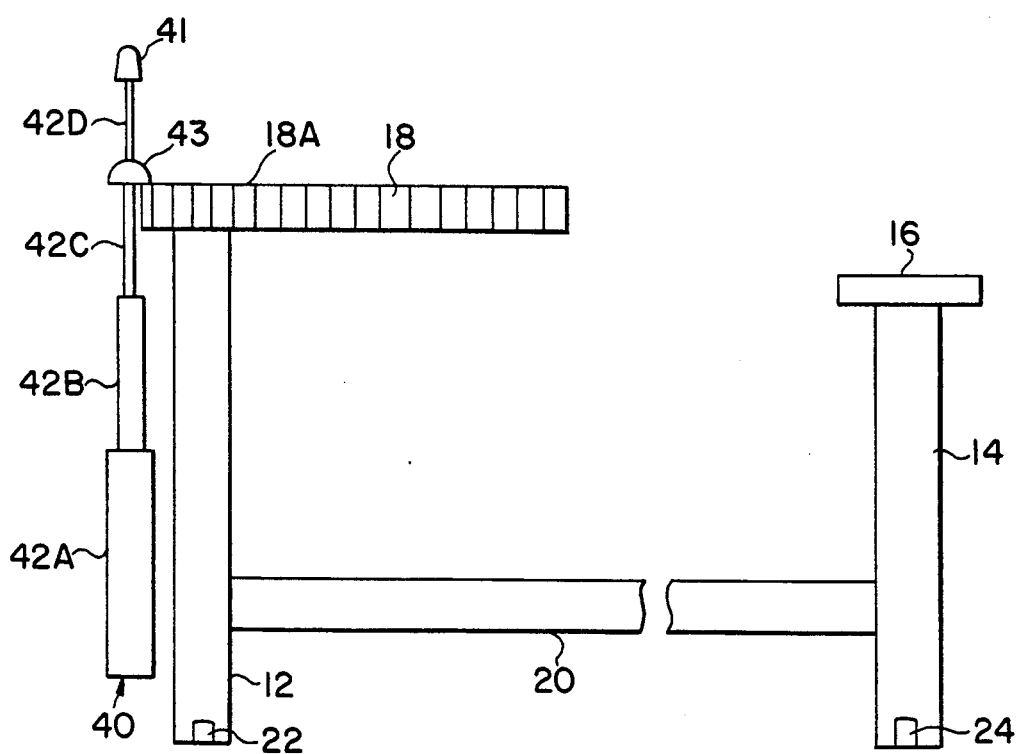
FIG. 2 is a side elevational view showing the target resting on the top edge of the arcuate member.

For measuring eye movement of a subject it is necessary for the subject to place his or her chin on the chin support 16 and face the arcuate member 18. The person conducting the test then requests the subject to follow a colored tip 41 of a target 40 with the eyes as the target is moved along the arcuate member away from the midpoint. When measuring the subject's smooth eye movement (e.g., in measuring ocular-pursuit), a notation is made as to the distance to the nearest half inch that the eye has moved from the midpoint of the arcuate member with smooth eye movement. The test is then repeated moving the target away from the midpoint in the opposite direction. The test is preferably done with each of the eyes of the subject separately and then with both eyes together. Further details of ocular-pursuit measuring are set forth in my U.S. Pat. No. 4,818,097, incorporated herein by reference. The apparatus shown in FIGS. 1 and 2 may also be used for other types of measurements involving eye movement.

The target 40 includes an elongated stem member and a colored tip 41 secured to the upper end of the stem. A support member 43 includes a flat bottom surface which can rest upon the upper edge surface 18A of the arcuate member 18, as illustrated for example in FIG. 2. Thus, by resting the bottom surface of the support member of the target on the upper edge surface of the arcuate member, the target can be moved very easily and smoothly along the arcuate member by the person doing the testing. This avoids the jerky or unsteady movement of the target which can sometimes happen.

Preferably the stem on which the colored tip or visual member of the target is secured is extensible. For example, it may include telescoping sections 42A, 42B, 42C and 42D, if desired.

Preferably the tip 41 of the target extends above the support member (for example, about two inches), as illustrated. The tip is colored (e.g., orange or tangerine) to make it easy to be seen by the subject.

Although it would be possible to mount a visual target (e.g., a ball or block) onto a track extending along the arcuate member, this would require more expensive apparatus and would be a more complicated arrangement. For example, a colored ball could be mounted on a cord extending along the top edge of the arcuate member, with the cord being operatively attached to a dial or a rotating knob on the arcuate member. Thus, by rotating the dial or knob the target could be caused to move along the arcuate member.

As another alternative, the support member could be a block having a square or rectangular cross-section. It may have a flat or planar bottom edge which can rest upon the upper edge of the arcuate member.

As another alternative, the support member could be a cone member having a flat bottom surface, as illustrated.

The size and shape of the support member may vary as long as it includes a bottom surface which allows it to rest upon the upper edge of the arcuate member. Generally, the bottom surface of the support member should be flat, as illustrated, although other shapes could also be used as long as the support member is able to rest upon the upper edge of the arcuate member. For example, the support member could include an arm or finger projecting outwardly to rest upon the arcuate member or in a groove in the arcuate member. The bottom of the support member may be open or closed as long as it is capable of resting on the arcuate member as it is moved along.

Other variants are possible without departing from the scope of the invention.

What is claimed is:

1. A technical process for measuring the ocular tracking ability of a person comprising the use of the following:
   (a) providing an ocular-pursuit measuring instrument comprising:
      (i) a first upstanding leg member;
      (ii) a second upstanding leg member spaced from the first leg member;
      (iii) connecting means connecting said first and second leg members;
      (iv) vertically adjustable chin support means at the upper end of said first leg member, said support means being adapted to stably support said person's head; and
      (v) an arcuate member pivotably mounted at its midpoint to the upper end of said second leg member in a manner such that said arcuate member may be pivoted about an axis passing through said midpoint perpendicular to the axis of said second leg member; wherein said arcuate member includes a graduated scale therealong; wherein said arcuate member includes an upper edge surface;
   (b) positioning such person in a manner such that the person's chin is stably supported by said chin support means;
   (c) placing said arcuate member in a horizontal position;
   (d) testing the person's ocular tracking ability by moving a target along said arcuate member from said midpoint to measure smooth eye movement by such person following said target; wherein said target comprises an elongated stem having an upper end, a colored tip secured to said upper end, and a support member attached to said stem member below said colored tip, wherein said support member includes a seat which enables said support member to be supported on said upper edge surface of said arcuate member; and
   (e) recording the number of units on said graduated scale between said midpoint and the maximum point where smooth eye movement was completed accurately.

2. A process in accordance with claim 1, wherein step (d) comprises:
   (i) moving said target along said arcuate member from said midpoint until a first point of nystagmus is observed;
   (ii) returning said target to said midpoint;
   (iii) moving said target along said arcuate member from said midpoint, while measuring smooth eye movement, to a point which is less than said first point of nystagmus;
   (iv) returning said target to said midpoint;
   (v) moving said target along said arcuate member from said midpoint, while measuring smooth eye movement, to a point which is one graduated unit farther than the point reached in step (iii);
   (vi) repeating steps (iv) and (v), increasing the distance said target is moved along said arcuate member by one graduated unit with each repetition until a second point of nystagmus is reached.

3. A process for measuring improvement in the ocular tracking ability of a person undergoing motor perceptual training, comprising the steps of:
   (a) providing an ocular-pursuit measuring instrument comprising:
      (i) a first upstanding leg member;
      (ii) a second upstanding leg member spaced from the first leg member;
      (iii) connecting means connecting said first and second leg members;
      (iv) vertically adjustable chin support means at the upper end of said first leg member, said support means being adapted to stably support said person's head; and
      (v) an arcuate member pivotably mounted at its midpoint to the upper end of said second leg member in a manner such that said arcuate member may be pivoted about an axis passing through said midpoint perpendicular to the axis of said second leg member; wherein said arcuate member includes a graduated scale therealong; wherein said arcuate member includes an upper edge surface;
   (b) measuring the ocular tracking ability of said person with said instrument prior to administering motor perceptual training; said measuring comprising the steps of:
      (i) positioning such person in a manner such that the person's chin is stably supported by said chin support means;
      (ii) placing said arcuate member in a horizontal position;
      (iii) testing said person's ocular tracking ability by moving a target along said arcuate member from said midpoint to measure smooth eye movement by such person following said target; wherein said target comprises an elongated stem having an upper end, a colored tip secured to said upper end, and a support member attached to said stem member below said colored tip, wherein said support member includes a seat which enables said support member to be supported on said upper edge surface of said arcuate member; said testing comprising the steps of:
         (1) moving said target along said arcuate member from said midpoint until a first point of nystagmus is observed;
         (2) returning said target to said midpoint;
         (3) moving said target along said arcuate member from said midpoint, while measuring smooth eye movement, to a point which is less than said first point of nystagmus;
         (4) returning said target to said midpoint;
         (5) moving said target along said arcuate member from said midpoint, while measuring smooth eye movement, to a point which is one graduated unit farther than the point reached in step (3);
         (6) repeating steps (4) and (5), increasing the distance said target is moved along said arcuate member by one graduated unit with each repetition until a second point of nystagmus is reached;

(iv) recording the number of units of said graduated scale between said midpoint and the maximum point where smooth eye movement was completed accurately;

(c) administering motor perceptual training to said person; and (d) re-measuring the ocular tracking ability of said person following said training by repeating steps (b) (i) through (b) (iv).

4. A process for diagnosing a person's need for motor perceptual training comprising the steps of:

(a) providing an ocular-pursuit measuring instrument comprising chin support means facing the midpoint of an arcuate member spaced therefrom; wherein said chin support means is adapted to stably support such person's head; wherein said arcuate member is pivotably mounted at its midpoint; and wherein said arcuate member includes a graduated scale therealong; wherein said arcuate member includes an upper edge surface;

(b) positioning such person in a manner such that the person's chin is stably supported by said chin support means;

(c) placing said arcuate member in a horizontal position;

(d) testing the person's ocular tracking ability by moving a target along said arcuate member from said midpoint to measure smooth eye movement by said person following said target; wherein said target comprises an elongated stem having an upper end, a colored tip secured to said upper end, and a support member attached to said stem member below said colored tip, wherein said support member includes a seat which enables said support member to be supported on said upper edge surface of said arcuate member; and (e) recording the number of units on said graduated scale between said midpoint and the maximum point where smooth eye movement was completed accurately.

5. A process in accordance with claim 4, wherein said support member has an inverted cone shape.

6. A process in accordance with claim 4, wherein said stem member is extensible.

* * * * *